July 8, 1958 T. CARLILE Plant Pat. 1,729
ANCHUSA PLANT
Filed Oct. 25, 1957
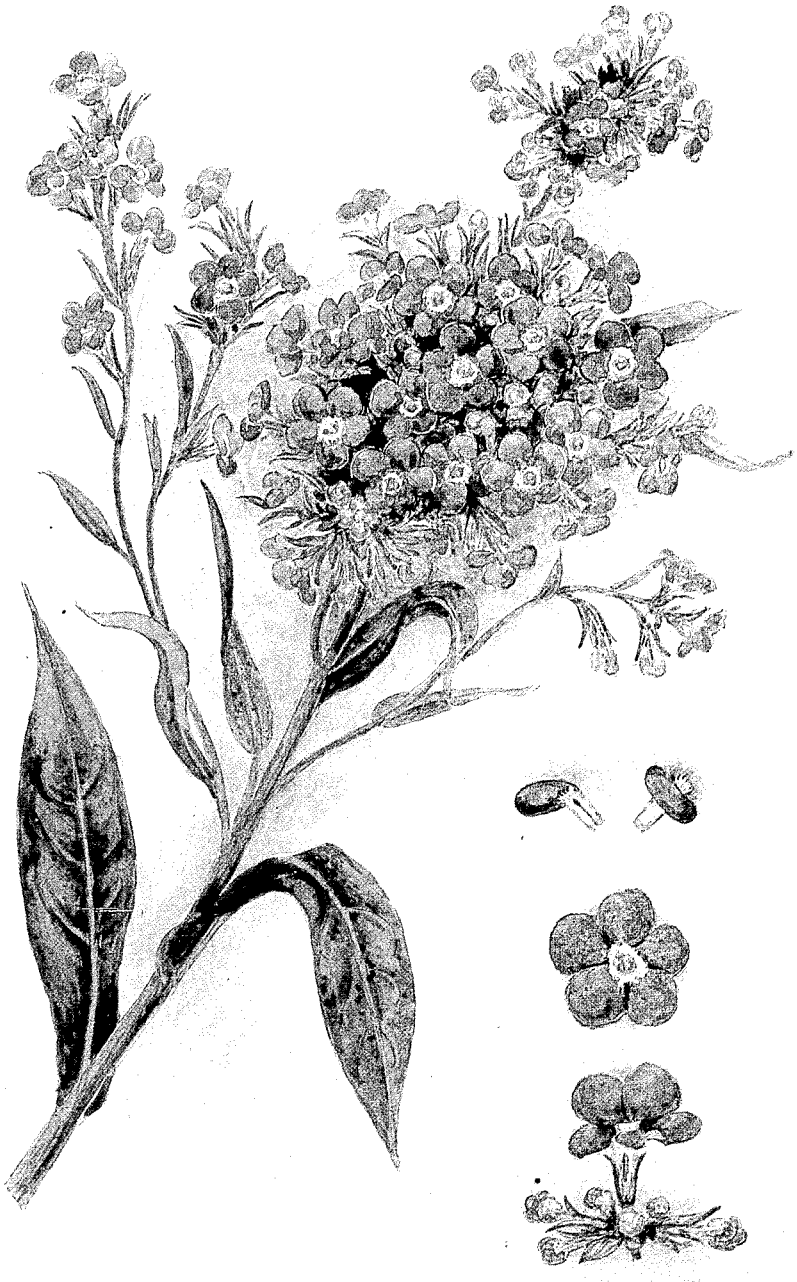
WITNESS
Addison E. Avery
INVENTOR
Thomas Carlile, deceased,
by Wendy Veronica Carlile, adm.,
by John H. Lemmon,
her ATTY.

United States Patent Office

Plant Pat. 1,729

Patented July 8, 1958

1,729

ANCHUSA PLANT

Thomas Carlile, deceased, late of Twyford, England, by Wendy Veronica Carlile, administratrix, Berkshire, England, assignor to John J. Grullemans, Cleveland, Ohio Application October 25, 1957, Serial No. 692,509

1 Claim. (Cl. 47—60)

This invention relates to a new and distinct variety of anchusa plant.

The new variety was first developed by me at Twyford, North Reading, Berkshire, England, and was there asexually reproduced by me by root cuttings.

The new variety of plant was developed in the following manner:

An *Anchusa italica* blue was crossed with one from several hundred previously selected seedlings of the anchusa plant known commercially as "Feltham Blue," an unpatented variety of English origin. From this crossing, selected seedings, as pollen parents, were again crossed with Feltham Blue. The present variety is a selected one of the seedlings from this latter crossing.

*The drawing*

The new variety is illustrated in the drawing in which the large central view shows a stalk of the plant with leaves, flowers, and buds. The small drawings in the lower right-hand corner, reading from top to bottom, are:

At the top left, an enlarged side elevation of a petal of a floret including a portion forming part of the trumpet, as viewed from the inside of the trumpet, and showing a single pistil and the white hairs defining the eye of the blossom; at the top right, a left side elevation of the portion of the floret shown at the top left; at center, a front elevation of one of the florets looking into the trumpet axially; and at bottom, a side elevation of one of the florets, together with a plurality of the buds in various states of bloom.

The color references herein are to the Maerz and Paul Dictionary of Color.

*Root*

The roots of the plant are normally openly branched, coarse, and of average size with the usual lateral spread. The plant is generally deep rooted. The winter resistance of the roots, when unprotected, is very good as they have withstood temperatures as low as zero degrees Fahrenheit, in England. The root, for effective growth, appears to prefer medium loam.

*Exposed plant*

The exposed plant structure, as a whole, is in the form of an herbaceous, upright, bushy, hardy perennial of compact growth, having a somewhat rounded top. It grows to about two and one half feet in height for a one to three year old plant and this dwarfed habit of sturdy, upright growth is one of its desirable and characterizing features. The bush, in general, is symmetrical and oval. It has withstood temperatures as low as zero degrees Fahrenheit unprotected. It appears to have a high resistance to drought and wetness. It prefers moderate sun to partial shade but will grow in any exposure. Further, it prefers a well-drained or normal soil of almost any type except a heavy wet clay.

*Main stalks and branches*

The main stalks grow upright and are very much branched. They are relatively stiff and adequate to support the foliage and bloom well. The color of the new growth is a soft green, Plate No. 20–L–7, and the old growth somewhat darker. The main stalks average about two and one half feet in length from the soil level to the tip, and grow in group arrangement from the roots. Their surface is rather prickly and hairy.

The branches are alternate with a hirsute surface texture. They are very thick growing and relatively stiff, and are adequate to support the bloom, foliage and fruit well.

*Foliage*

The foliage is generally compact, the leaves being arranged oppositely and average in quantity. On top, the new leaves are a light yellowish green comparable to Plate No. 20–L–7, the underside being a slightly paler green comparable to Plate No. 20–H–4. The leaves have a heavy midrib on both the face and underside, which is a light yellowish green, comparable in color to Plate No. 20–K–3. The color of the foliage and stems at the base of the florets is Marron Glacé, comparable to Plate 14–A–8. The color of the leaves is relatively uniform for old leaves and new leaves.

The leaves are about average in size, reaching a maximum length of about nine inches and a minimum length of about three to four inches, with a maximum width of one and a half inches and a minimum width of one half inch. They are ovate with entire margins with a tapering base and mucronate apex. The leaves are of medium thickness with hirsute upper and lower faces. Their persistency on the plant is good. They are, in general, usual for this type of plant. The pedicels average about one inch in length and are quite strong and have a hirsute surface texture. They are free from stipules.

*The flower*

The blooming of the plant appears to be little affected by its geographical range as it seems to do well where the temperatures range from about one degree Fahrenheit to ninety degrees Fahrenheit.

For blooming, the plant prefers the sun with a southern or western exposure and a moderately dry, hot season in well-drained acid or neutral soil. It prefers, for most effective blooming, a relatively rich loam or sandy loam. There appears to be little change in the quality or quantity of the bloom under changes in the conditions above except that the best color is obtained in sunny, warm locations, the number and size of blooms being little affected by changes in sun, shade, moisture, heat, cold, and the like, only the color apparently being affected.

The plant blooms from April continuously throughout the summer.

The buds are extra large and elongated. They are borne upright on the terminals and are deep blue in color when the sepals first divide, turning to a more or less gentian blue when the petals begin to unfurl, and then becoming a deep blue again when half blown.

The calyx is of average size and of the usual surface texture for anchusa plants. The peduncles average from one half to one inch in length and are otherwise usual, being soft green in color and of medium strength. The pedicels of the florets average from one quarter to one half inch in length and are of the usual texture and color. They are of medium strength. The buds open more rapidly when the temperature of the season is higher.

The florets average, from tip to tip of petals, about one to one and a half inches in diameter. There are literally hundreds of florets per plant. They are borne in racemes. Their permanence on the plant is good, as evidenced by the long blooming period from April throughout the summer. The florets have the usual number of five petals. A desirable and characterizing feature of the plant is the exceptional blue color of the petals, comparable to Plate No. 41–C–11, with the base of the petals a somewhat pinkish cast, such as a phlox pink, Plate No. 41–F–3. The inside of the petals is substantially the same color as the outside. The reverse of the petals also is a comparable blue. The general tonality of the blooms from a distance is a beautiful dense gentian blue.

Tiny grey-white hairs on each of the five single petals form a grey-white eye at the center of each floret. Other than as above pointed out, the petals and florets have the usual characteristics of anchusa plant florets. The blooms have a faint fragrance. Each has five stamens in the tube of the corolla, the stamens being bluish white with filaments of medium length and whitish color. The pollen is a pale yellow. The pistil is brown tipped with a purple stem. The styles have a very small pinhead.

The fruit is of the usual type, being about medium in size supported on short and strong stems. The skin of the fruit is thin but not tough. The flesh has a crisp quality. At maturity, the fruit has the usual color and it is borne in the usual clusters.

The plant is adaptable to many climates and to almost any soil except wet, heavy clay. The geographical range does not appear to be limited except where the seasons are extremely wet.

The plant is characterized particularly by its dwarfed but sturdy and upright habit of growth to a height of only about two and one half feet, its exceptionally large flowers of very intense and most desirable blue, its early blooming in the season and its long blooming period. In all of these characteristics, it differs entirely from other varieties of anchusa plants.

Having thus described my invention, I claim:

The new and distinct variety of anchusa plant substantially as herein shown and described.

No references cited.